United States Patent [19]

Butter

[11] 4,245,115

[45] Jan. 13, 1981

[54] SELECTIVE CARBONYLATION OF OLEFINICALLY UNSATURATED HYDROCARBONS USING PALLADIUM-ARSINE OR -STIBINE CATALYSTS

[75] Inventor: Stephen A. Butter, Cherry Hill, N.J.

[73] Assignee: Mobil Oil Corporation, New York, N.Y.

[21] Appl. No.: 833,194

[22] Filed: Sep. 14, 1977

Related U.S. Application Data

[63] Continuation-in-part of Ser. No. 577,362, May 14, 1975, abandoned, which is a continuation-in-part of Ser. No. 447,709, Mar. 4, 1975, abandoned, which is a continuation-in-part of Ser. No. 8,699, Feb. 4, 1970, abandoned.

[51] Int. Cl.$^3$ .............................................. C07C 67/38
[52] U.S. Cl. ................................. 560/233; 560/130; 562/522; 260/544 A
[58] Field of Search ............... 560/233, 130; 562/522

[56] References Cited

U.S. PATENT DOCUMENTS

| | | | |
|---|---|---|---|
| 3,102,899 | 9/1963 | Connell | 260/533 AN |
| 3,168,553 | 2/1965 | Slaugh | 560/233 |
| 3,437,676 | 4/1969 | Kutepow | 560/233 |
| 3,530,168 | 9/1970 | Biale | 560/233 |
| 3,641,074 | 2/1972 | Fenton | 560/233 |
| 3,641,076 | 2/1972 | Booth | 560/233 |
| 3,668,249 | 6/1972 | Fenton | 560/233 |
| 3,733,362 | 5/1973 | Biale | 560/233 |
| 3,755,421 | 8/1973 | Fenton | 560/233 |
| 3,839,378 | 10/1974 | Yamaguchi | 560/233 |
| 3,857,900 | 12/1974 | Wilkinson | 560/233 |

FOREIGN PATENT DOCUMENTS 2739096  3/1978  Fed. Rep. of Germany .
48-13088  4/1973  Japan .

*Primary Examiner*—Natalie Trousof
*Assistant Examiner*—Michael Shippen
*Attorney, Agent, or Firm*—Charles A. Huggett; Howard M. Flournoy

[57] ABSTRACT

A carbonylation process is provided for conversion of olefinically unsaturated hydrocarbons to a mixture of esters or acids with a high ratio of iso:normal ester or acid by reaction with carbon monoxide and a hydroxylic compound, said process being carried out in the absence of added hydrogen or oxygen and in the presence of a palladium salt complexed with an arsine or stibine ligand as catalyst; 2–10 additional moles of arsine or stibine ligand per mole of catalyst may be present in said process to further enhance the ratio of iso:normal product and to promote catalyst stability. The catalyst, for example, may be palladium dichloride bis(triphenylarsine) or palladium dichloride bis(tri-p-tolyl arsine).

12 Claims, No Drawings

SELECTIVE CARBONYLATION OF OLEFINICALLY UNSATURATED HYDROCARBONS USING PALLADIUM-ARSINE OR -STIBINE CATALYSTS

CROSS-REFERENCE TO RELATED APPLICATIONS

This is a continuation-in-part of Ser. No. 577,362, filed May 14, 1975 now abandoned which is a C-I-P of Ser. No. 447,709, filed Mar. 4, 1975 now abandoned which was a C-I-P of Ser. No. 8,699, filed Feb. 4, 1970 now abandoned all of which having been entitled Selective Carbonylation of Olefinically Unsaturated Hydrocarbons using Palladium-Arsine or -Stibine Catalysts.

BACKGROUND OF THE INVENTION

1. Field of the Invention

This invention relates to a process of carbonylation of olefinically unsaturated hydrocarbons to a mixture of esters or acids with a high ratio of iso:normal ester or acid of at least about 3:1, said process being carried out in the presence of a palladium salt complexed with an arsine or stibine ligand as catalyst. More particularly, it relates to a process of carbonylation of olefinically unsaturated hydrocarbons by reaction with carbon monoxide and a hydroxylic compound, e.g., alcohols, phenols or water, without the addition of external hydrogen or oxygen, in the presence of the above-disclosed catalyst to yield a mixture of esters or acids with a high ratio of iso:normal ester or acid. This invention also relates to a process wherein 2-10 moles of arsine or stibine ligand per mole of catalyst are utilized to stabilize said catalyst. The specific amount so utilized varies with reaction conditions.

SUMMARY OF THE PRIOR ART

It is generally known that olefins, carbon monoxide and alcohols or water may be combined to form carboxylic acids or esters using catalysts based on Group VIII metals which form carbonyls.

Early carbonylation processes based on nickel catalysts utilized vigorous reaction conditions and were accompanied by side reactions (W. Reppe, Liebigs Ann. Chem. 582,1 [1953]). Octacarbonyldicobalt has also been used to form carboxylic acids (R. Ercoll, Das 1092015, [1957] Montecatini).

There is also known a carbonylation process conducted under mild conditions with minimum by-product formation which is based on palladium complex salts as catalysts, examples of which include palladium catalyst containing phosphines, phosphites, ammonia, amines, nitriles and unsaturated hydrocarbons as ligands (vonKutepow, et al. U.S. Pat. No. 3,437,676).

Also, the use of palladium dichloride in an alcoholic solution of hydrogen chloride is known to convert olefins into esters (J. Tsuji, et al. Tetrahedron Letters [1963] 1437).

In prior art known to the inventor, carbonylation of terminal of alpha olefins such as propylene results in mixtures of esters or acids such that the ratio of iso to normal was usually about 1:1 or less to about 2:1.

SUMMARY OF THE INVENTION

In accordance with this invention, there is provided a carbonylation process using a palladium salt complexed with an arsine or stibine ligand as catalyst in which olefinically unsaturated hydrocarbons are catalytically converted in the absence of added hydrogen or oxygen to a mixture of esters or acids with a high ratio of at least about 3:1 and preferably from about 5:1 to about 20:1 iso to normal ester or acid by reaction with carbon monoxide and a hydroxylic compound wherein increased catalyst stability, prolonged catalyst life and an increased reaction rate are made possible. It is understood that this invention is directed to terminal or alpha-olefins of at least three carbon atoms, carbonylatable to mixtures of iso and linear esters or acids, thus symmetrical olefins including ethylene are not within its scope. Therefore this invention more particularly is limited to only those olefins carbonylatable to or capable of being carbonylated to a mixture of iso and normal ester or acid carbonyls.

Accordingly the present invention utilizing a palladium salt complexed with for example an arsine ligand, i.e., palladium-arsine, provides carbonylation as in the case of propylene, to butyric acid esters (e.g. methyl isobutyrate-MIB and methyl-n-butyrate-MB) with the ratio of iso:normal ester of, for example, generally better than 5:1 and in certain selected cases above 10:1. Furthermore as mentioned hereinabove the catalytic processes described herein provide iso:normal ratios of at least about 3:1 and usually from about 5:1 to about 20:1.

In prior art hydroformylation reactions, wherein related metal-catalyzed reactions of olefinically unsaturated hydrocarbons with carbon monoxide and hydrogen were studied with emphasis placed on improving the selectivity of straight (normal) rather than branched (iso) chain products, arsines were noted as promoting selectivity for "normal" rather than "iso" products. Such hydroformylation processes used catalysts of metal salts complexed with ligands containing trivalent arsenic and similarly trivalent phosphorous or trivalent antimony to increase the ratio of normal:iso. One would therefore expect arsines or stibines to have the effect of yielding a low ratio of iso:normal ester in carbonylation reactions of olefinically unsaturated hydrocarbons. However, surprisingly the opposite effect was found by applicant.

Further, the effect of increasing organophosphine basicity in hydroformylation reactions is to increase the selectivity to straight (normal) chain isomers. The opposite effect is found, as embodied herein, in the arsine- or stibine-ligated carbonylation reactions (e.g., use of catalyst with a more basic or electropositive arsine or stibine ligand increases the selectivity to branched [iso] chain isomers). For example, the ligand triphenylstibine can provide a ratio of MIB/MB of up to about 20:1.

Non-limiting examples of the olefinically unsaturated hydrocarbons which may be carbonylated according to the present invention are: propylene, butene-1, pentene-1, hexene-1, dienes, and trienes having terminal unsaturation and, in more general aspect, olefinically unsaturated hydrocarbons of from 3 to about 20 carbon atoms.

Hydroxylic compounds may be used, if desired, in the practice of the present invention. If a hydroxylic compound is used it may be one of several possibilities with the end product type being determined by the compound used. If alcohol is used, an ester is formed by the present process. If water is used, the product is an acid. Phenols may be used with the products being esters. If no hydroxylic media is used, the products may be acyl chlorides.

Additionally, any general purpose solvent may be used, if desired, in the process of the present invention. However, the use of certain selected solvents is preferred. Non-limiting examples of such solvents are: alcohols, phenols and water. Also suitable are ketones, esters, ethers and aliphatic, aromatic and heterocyclic hydrocarbons, and other materials inert under the conditions of practice of the present process.

If a solvent is used in the process of the present invention, an important factor to be considered in the selection of one suitable for the particular carbonylation reaction in question is the boiling point increment between the solvent and the product. For example, p-xylene is a preferred solvent in the reaction which yields methyl butyrate esters since these esters boil 25°-35° C. below the solvent. This boiling point difference enables efficient separation of the solvent and product by simple distillation.

The reaction temperature during the process of the present invention may be varied over a rather wide range, for example, in the range of from about 20° C. to about 200° C. Temperatures between 60° C. and 100° C. and from 70°-90° C. are especially preferred to assist in catalyst stability with concomitant improvement in conversion.

The catalyst concentration used in the present invention may be varied over a wide range. However, a concentration varying from as low as 0.001% to about 50% or more, is useful with the range of from about 0.1 to about 5% (based on the weight of the unsaturated hydrocarbon reactant) being preferred. With the addition of from about 2–10 moles of arsine or stibine ligand as detailed below, catalyst stability is improved.

The process according to the present invention may be carried out under pressure sufficient to maintain the reactants in liquid phase. Depending upon the reactants used (i.e., the olefinically unsaturated hydrocarbon and hydroxylic compound), the pressure may vary between atmospheric to about 10,000 psig. In general, pressures of from about 50 to about 1500 psig are preferred and used.

In the practice of the carbonylation process of the present invention, the olefinically unsaturated hydrocarbon is reacted with carbon monoxide and a suitable hydroxylic compound as described above, e.g., an alcohol, in the presence of a catalyst of the formula $L_mPdX_p$, wherein L is selected from the group consisting essentially of organo-arsine, organo-stibine, and X is an acid function. A suitable solvent is usually, although not necessarily, present. The catalyst may, for example, be formed in-situ by exchanging the arsine or stibine ligand with that in the labile $PdCl_2[As(C_6H_5)_3]_2$ or $PdCl_2[Sb(C_6H_5)_3]_2$ complex or similar species.

The above-mentioned acid function, X, of the catalyst of the process of the present invention may be any one of several acid functions with halide radicals and particularly the chloride radical preferred. Non-limiting examples of acid functions which may be present in the catalyst of the present invention include chloride, bromide, iodide, sulfate, phosphate, acetate, nitrate, propionate, borate, and others.

Excess amounts of arsine or stibine ligand is previously mentioned over that amount required to form the complex are used in certain instances to stabilize the catalyst and, in some cases, with obtainment of increased yields of desired product.

The use of the palladium arsine or palladium stibine catalyst is valuable also for directing the course of carbon monoxide addition to an olefinic double-bond and is, therefore, particularly useful for preparing methyl isobutyrate from propylene. Methyl isobutyrate may be oxidatively dehydrogenated to form methyl metacrylate, a valuable monomer used in resin production.

The reaction may be carried out in the presence, if desired, of hydrohalic acids, particularly of hydrogen chloride. It is advantageous to have hydrohalic acids present because lower temperatures may be used at a given catalyst concentration, or lower catalyst concentrations at a given temperature. The concentration of the acid, e.g. hydrogen chloride is carefully controlled to insure relatively mild conditions, e.g., from about 60°-100° C. and from about 850-1500 psig (see Table I also). The acids are generally used in amounts of up to about 10% by weight, i.e. from about 0.05 to about 10%. They may be used in alcoholic or aqueous solution, but optionally also in pure form.

DESCRIPTION OF SPECIFIC EMBODIMENTS

The following examples illustrate the process of the present invention. The results summarizing Examples 1-11 are shown in Table I below.

EXAMPLE 1

A 300 cc. Hastellow autoclave was charged with 22.6 g. methanol, 0.45 g. hydrogen chloride, 0.562 g. palladium dichloride bis (triphenylarsine) and 43.1 g. of p-xylene. Twenty grams of liquid propylene were pumped in and stirring was started. The temperature was brought to 90° C. and the autoclave was pressured with carbon monoxide to 1000 psig. After 4.5 hours during which time 190 psi was absorbed, the reaction mixture was cooled. The products were distilled and analyzed by gas chromatography. The yield based on reacted propylene was practically quantitative and consisted of 8.45 g. of methyl isobutyrate and methyl n-butyrate in a ratio of 84 parts to 16 parts.

EXAMPLE 2

Following the procedure of Example 1, twenty grams of propylene were added to 0.562 g. palladium dichloride bis(triphenylarsine), 0.430 g. triphenylarsine, 0.10 g. hydrogen chloride and 15.2 g. of methanol in 43.1 g. p-xylene. The autoclave was heated to 85° C. and carbon monoxide was added to give a total pressure of 1000 psig. After 3.75 hours, 10.2 g. of methyl butyrate esters were formed in a ratio of 87 parts of iso- to 13 parts normal.

EXAMPLE 3

The reactants were identical to those in Example 2, but 1.075 g. triphenylarsine was added and the temperature was 80° C. The reaction mixture contained 15.55 g. of methyl butyrate esters in a ratio of 87 parts iso- to 13 parts normal.

EXAMPLE 4

Following the procedure of Example 1, 20 grams of propylene were added to 0.562 g. of palladium dichloride bis (triphenylarsine), 2.17 g. triphenylarsine, 0.10 g. hydrogen chloride and 20.6 g. methanol in 43.1 g. of p-xylene. Carbon monoxide was added at 80° C. to maintain the pressure at approximately 900 psig. After 6 hours, the reaction mixture contained 30.2 g. methyl butyrate esters in the proportion 83 parts iso- to 17 parts normal.

EXAMPLE 5

As in Example 1, 13.3 g. liquid propylene were added to 0.562 g. palladium dichloride bis (triphenylarsine) and 0.1 hydrogen chloride in 67.5 g. of methanol. After about 6 hours, one hour at 70° C., two at 85° C. and three at 90° C., a two percent yield of methyl butyrate esters in an 83:17 iso:normal ratio was found.

EXAMPLE 6

An autoclave was charged with 33.3 g. pentene-1, 15.2 g. methanol, 0.10 g. hydrogen chloride, 0.562 g. palladium chloride bis (triphenylarsine) and 43.8 g. 1,2,4-trimethylbenzene. Carbon monoxide was added to 900 psig. and the temperature brought to 90° C. After 6.5 hours, the mixture was cooled and analyzed two grams of esters consisting of 78 parts methyl 2-methyl pentanoate and 22 parts methyl n-hexanoate.

EXAMPLE 7

The procedure of Example 2 was followed but with 0.84 g. bis (diphenylarsino) methane instead of triphenylarsine as added ligand. Carbon monoxide was added to 940 psig. at 80° C., and the autoclave stirred overnight. The product analyzed for 13.8 g. of methyl butyrate esters containing 91.4 parts iso- and 8.6 parts normal.

EXAMPLE 8

The procedure of Example 2 was followed but 1.09 g. tri-p-tolyl arsine was substituted for triphenylarsine as added ligand. Carbon monoxide was added at 80° C. to maintain total pressure at about 950 psig. for five hours. The products consisted of 24 grams of methyl butyrate esters containing 87.9 parts iso and 12.1 parts normal ester.

EXAMPLE 9

The procedure of Example 2 was followed but 2.50 g. triphenyl stibine added to replace triphenylarsine. Carbon monoxide was added to 1000 psig. total and the temperature maintained overnight at 80° C. About two grams of ester product was found consisting of in excess of 95 parts methyl isobutyrate, the remainder being methyl-n-butyrate.

EXAMPLE 10

For comparison with the analogous phosphine complex, conditions similar to those in Example 1 were followed with 0.50 g. palladium di chloride bis (triphenylphosphine) in place of the arsine ligand. The temperature was 90° C. and carbon monoxide was replenished to maintain pressure at 1000 psig. After 4.5 hours the reaction mixture analyzed 23.4 g. of methyl isobutyrate and methyl n-butyrate in a ratio of 54 parts to 46 parts.

EXAMPLE 11

As in Example 4, twenty grams of propylene were added to 0.562 g. palladium chloride bis (triphenylarsine), 1.82 g. triphenylphosphine, 0.10 g. hydrogen chloride and 15.2 g. methanol in 43.1 g. p-xylene. Carbon monoxide was added at 90° C. to 1000 psig. total pressure. After six hours 0.3 g. methyl butyrate esters were found in the ratio 25 parts iso- to 75 parts normal.

One may note from the data of the examples as set forth herein that the carbonylation process of the present invention provides products with a higher ratio of iso:normal ester when an appropriate hydroxylic compound is reacted with an olefinically unsaturated hydrocarbon and carbon monoxide. Example 10 shows that carbonylation of propylene with the use of the prior art catalyst, palladium dichloride bis (triphenylphosphine), as a catalyst only provides a low ratio of 1.17:1, iso:normal ester product, whereas Examples 1 through 3 show that the use of palladium dichloride bis (triphenylarsine), as embodied for use in the present invention, illustrate dramatically that product ratios of from 5.25:1 to 6.69:1, are obtained when the olefinically unsaturated hydrocarbon is propylene. Example 9 further shows that the use of palladium dichloride bis (tri-phenyl-stibine), also embodied for use in the present invention, provides a product ratio of 19:1. Use of other organoarsine or stibine ligands also show high product ratios of iso:normal ester, see in particular Examples 7 and 8. Example 11 shows that when the reaction mixture contains prior art triphenylphosphine at the predominant catalyst, the carbonylation reaction provides a low product ratio of 0.33:1 of iso to normal product.

The data detailed hereinbelow and in Table II illustrate the improved catalyst stability, prolonged catalyst life and increased rate or reaction when the carbonylation reaction conditions are such as to require affirmative means as embodied herein to inhibit catalyst deactivation under such conditions.

In the catalytic carbonylation of an alpha olefin, e.g., propylene, and esterification with methanol to give methyl iso- and n-butyrates as disclosed, emphasis has been to further increase the iso-normal ester ratio modified by use of palladium-arsine catalysts. However, the catalyst-life of these systems under certain reaction conditions tended to be less stable than those with the analogous phosphine catalyst. It has been now discovered that the addition of 2 or more additional moles of arsine or stibine ligand per mole of catalyst to the reaction tends to increase catalyst stability under such conditions, i.e., higher temperatures greater than about 90° C. and where carbon monoxide is absorbed by the catalyst at a rapid rate, i.e., at pressures of about 100 psig or more of CO whereby the catalysts tends to be deactivated. Catalyst deactivation proceeds by loss of ligands, L, and an eventual reduction by carbon monoxide to palladium metal.

TABLE I

| | CARBONYLATION OF OLEFINICALLY UNSATURATED HYDROCARBONS | | | |
|---|---|---|---|---|
| Example | Olefinically Unsaturated Hydrocarbon | Ligand | Reaction Temperature/ Pressure (°C./psig.) | Product Ratio (iso:normal ester) |
| 1 | propylene | triphenylarsine | 90/1000 | 5.25:1 |
| 2[1] | propylene | triphenylarsine | 85/1000 | 6.69:1 |
| 3[1] | propylene | triphenylarsine | 80/1000 | 6.69:1 |
| 4[1] | propylene | triphenylarsine | 80/900 | 4.88:1 |
| 5 | propylene | triphenylarsine | */1000 | 4.88:1 |
| 6 | pentene-1 | triphenylarsine | 90/900 | 3.54:1 |

TABLE I-continued
CARBONYLATION OF OLEFINICALLY UNSATURATED HYDROCARBONS

| Example | Olefinically Unsaturated Hydrocarbon | Ligand | Reaction Temperature/ Pressure (°C./psig.) | Product Ratio (iso:normal ester) |
|---|---|---|---|---|
| 7 | propylene | bis (diphenylarsino)methane | 80/940 | 10.61:1 |
| 8 | propylene | tri-p-tolyl arsine | 80/950 | 7.26:1 |
| 9 | propylene | triphenylstibine | 80/1000 | >19:1 |
| 10 | propylene | triphenylphosphine | 90/1000 | 1.17:1 |
| 11[(1)] | propylene | triphenylarsine | 90/1000 | 0.33:1 |

*One hour at 70° C., two at 85° C., and three at 90° C.
[(1)]Reaction mixture contains a large amount of triphenylphosphine external from the catalyst itself.

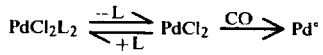

Increased catalyst stability is achieved under said conditions by two, five and ten additional moles of triphenyl arsine per mole of $PdCl_2(AsPh_3)_2$, i.e. 2–10 moles.

Catalyst lifetime is also enhanced and conversion raised on passing from the triphenyl arsine catalyst to tri-p-tolyl arsine. The latter catalyst give an increased rate of carbonylation probably due to the increased activation of carbon monoxide as a result of placing more electron density on palladium. The raised iso-normal ester ratio is apparently related to the increase in electron density on arsenic. In any event esterification with hydroxylic components such as methanol and tri-p-tolyl arsine leads to increased ratios of methyl isobutyrate in preference to methyl-n-butyrate. For example, the 5:1 MIB/MB ratio previously found was raised to 6.7:1 when hydrogen chloride concentration was lowered (Table II, runs 6 and 7) the change to the p-tolyl arsine further increased this ratio to 7.3:1. A further increase in MIB/MB ratio (to 10.6:1) was found when the more electropositive ligand, bis-(diphenylarsino) methane was used.

Table II is a summary of carbonylations having added moles of arsine. Pentene-1 carbonylation (Run 2) with a palladium dichloride-bis-triphenyl-arsine catalyst in pseudo-cumene solvent maintains good selectvity to the iso-ester, methyl 2-methylpentanoate, in contrast with the palladium phosphine experiment in methanol (Run 1). Use of substantial amounts of triphenyl phosphine for triphenyl arsine as in Run 3 resulted in the expected reversal of selectivity methyl-n-butyrate a normal product now being favored. They further illustrate that the use of the triphenylphosphine as the predominant catalyst promotes the formation of normal product rather than iso product as does the catalyst in accordance with his invention.

Further agreement with the electronic effect hypothesis noted above is found with the triphenylstibine complex catalyst (Run 5)*; the most electropositive ligand tested; the MIB/MB ratio was found to be approximately 20:1.
*Table II Examples 13, 14, 15 and 16 below carried under the following general conditions illustrate the effect of arsine relative to phosphine in raising the branched to linear product ratio.

Olefin (0.4 mole); alcohol (0.4 mole or 0.8 mole in case of $C_4H_6$); catalyst (0.007 mole); HCl (0.003 mole); solvent (40 grams); temperature 80°–90° C. and pressure 800–1000 psig.

EXAMPLE 12

Carbonylation of pentene-1 in methanol with $PdCl_2$ $(PPh_3)_2$-$CuCl_2(PPh_3)_2$ catalyst produced methyl-2-methyl pentanoate and methyl hexanoate in iso/n ratio of 56/44. With $PdCl_2$ $(PPh_3)_2$ in pseudo-cumene solvent iso/n ratio was 60:40. With $PdCl_2(AsPh_3)_3$ the iso/n ratio was raised to 78/22. Conditions were identical for all three carbonylations.

EXAMPLE 13

Carbonylation (rapid) of butene-1 in methanol solvent produced the following esters in quantitative yield at 83% conversion.

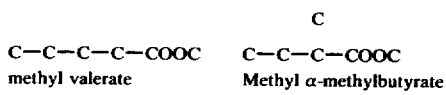

methyl valerate    Methyl α-methylbutyrate

The iso/n ratio with $PdCl_2(PPh_3)_2$ catalyst was 1.33/1. When PdCl [As(p-tolyl)$_3$]$_2$ was used a 4/1 iso/n ratio resulted.

EXAMPLE 14

Carbonylation (rapid) of cis-butene-2 in methanol solvent resulted in methyl α-methyl butyrate as the only

TABLE II
CARBONYLATION OF OLEFINICALLY UNSATURATED HYDROCARBONS WITH ADDED ARSINE

| RUN NO. | OLEFIN | CATALYST | REACTION TEMP., PRESSURE (°C. psig) | PRODUCT RATIO (ISO/N) |
|---|---|---|---|---|
| 1 | Pentene-1 | $PdCl_2(P\phi_3)_2$—$CuCl_2(PO_3)_2$ | 80/90 | 56/44 |
| 2 | Pentene-1 | $PdCl_2(As\phi_3)_2$ | 90/900 | 78/22 |
| 3 | Propylene | $PdCl_2(As\phi_3)_2 \cdot 10P\phi_3$ | 90/900 | 33/67 |
| 4 | Propylene | $PdCl_2(P\phi_3)_2$ | 90/750 | 54/46 |
| 5 | Propylene | $PdCl_2(As\phi_3)_2 \cdot 10Sb\phi_3$ | 80/1000 | >95/5 |
| 6 | Propylene | $PdCl_2(As\phi_3)_2 \cdot 2As\phi_3$ | 85/900 | 87/13 |
| 7 | Propylene | $PdCl_2(As\phi_3)_2 \cdot 5As\phi_3$ | 80/900 | 87/13 |
| 8 | Propylene | $PdCl_2(As\phi_3)_2 \cdot 10As\phi_3$ | 90/900 | 84/16 |
| 9 | Propylene | $PdCl_2(As\phi_3)_2 \cdot 2.5(\phi_2As)_2CH_2$ | 82/900 | 91/9 |
| 10 | Propylene | $PdCl_2(As\phi_3)_2 \cdot 5(p-CH_3C_6H_4)_3As$ | 80/1000 | 88/12 | product, when the catalyst was PdCl$_2$(AsPh$_3$)$_2$ or its phosphine equivalent.

EXAMPLE 15

Identical carbonylations of hexene-1 in methanol solvent using first PdCl$_2$(AsPh$_3$)$_2$ and then PdCl$_2$(PPh$_3$)$_2$ point up the superiority of the triphenylarsine catalyst system over the triphenylphosphine catalyst system. Use of the phosphine catalyst resulted in a ratio of branched to linear product of 45 to 55%, while in use of the arsine catalyst gave a branched to linear ratio of 83 to 17%. Thus the selectivity for branched product was raised from 45 to 83% by using the arsine catalyst instead of the phosphine catalyst.

Examples 12, 13 and 15 demonstrate the increased selectivity for branched versus linear products in embodiments according to this invention. The use of arsine and stibine versus phosphine catalyst as defined hereinabove directs carbonylation to the internal carbon atom resulting in increased branched product.

Example 14 illustrates the fact that symmetrical olefins are not within the scope of this invention and that if such olefins are processed in accordance with it the final product will not be a mixture of normal and iso-carbonyl containing compounds.

Although this invention has been described with preferred embodiments, it is understood that one of ordinary skill in the art may devise modifications and variations while nonetheless do not depart from the spirit and scope of the invention.

I claim:

1. A liquid phase process for the carbonylation of olefinically unsaturated hydrocarbon compounds carbonylatable to a mixture of iso and normal carbonyl-containing compounds by reacting an olefinically unsaturated hydrocarbon compound with carbon monoxide and a hydroxylic compound selected from the group consisting of alcohol, water and phenol in the presence of a palladium salt catalyst having the formula L$_m$PdX$_y$ in which L is a ligand member selected from the group consisting of phenyl or tolyl arsines and stibines, X is an acid function selected from the group consisting of halide, sulfate, phosphate, nitrate, borate, acetate, and propionate, m is an integer from 1 to 4 inclusive, and y is an integer or 1 or 2, the sum of m+y being an integer of from 2 to 6 inclusive wherein no external hydrogen or oxygen is added to said process and wherein said mixture of iso and normal carbonyl-containing compounds comprise iso and normal esters in a ratio of iso to normal of from about 3:1 to about 20:1 and wherein said carbonylation is carried out in the presence of 2–10 additional moles of said arsine or stibine ligand per mole of said catalyst.

2. A process as defined in claim 1 wherein the temperature is from about 60° C. to about 100° C.

3. A process as defined in claim 1 wherein the hydroxylic compound is an alcohol and the temperature is from about 70° C. to about 90° C.

4. A process as defined in claim 1, wherein the olefinically unsaturated hydrocarbon is terminally unsaturated and has from about 3 to about 20 carbon atoms.

5. A process as defined in claim 4 wherein said unsaturated hydrocarbon is propylene.

6. A process as defined in claim 5 wherein the ratio of iso:normal product is from about 5:1 to about 20:1.

7. A liquid phase process as defined in claim 1, comprising using as the catalyst a palladium salt having the formula L$_m$PdX$_y$ in which L is an arsine or stibine ligand member selected from the group consisting of phenyl- and tolyl-stibines and arsines.

8. A liquid phase process as defined in claim 7, comprising using as the catalyst a palladium salt having the formula L$_m$PdX$_y$ in which L is a ligand member selected from the group consisting of triphenylarsine, triphenylstibine, bis (diphenylarsino) methane and tri-p-tolyl arsine, and X is a halide.

9. A process as defined in claim 8 wherein the acid function is chloride.

10. A process as defined in claim 8, wherein the catalyst is palladium dichloride bis (tiphenylarsine).

11. A process as defined in claim 8, wherein the catalyst is palladium dichloride bis (tri-p-tolyl arsine).

12. A process as defined in claim 8, wherein the catalyst is palladium dichloride bis (phenylarsino) methane.

* * * * *